(12) United States Patent
Bednarke

(10) Patent No.: US 11,415,641 B2
(45) Date of Patent: Aug. 16, 2022

(54) DETACHABLE ARRANGEMENT FOR ON-SCALP MAGNETOENCEPHALOGRAPHY (MEG) CALIBRATION

(71) Applicant: HI LLC, Los Angeles, CA (US)

(72) Inventor: Zachary Bednarke, Los Angeles, CA (US)

(73) Assignee: HI LLC, Los Angeles, CA (US)

( * ) Notice: Subject to any disclaimer, the term of this patent is extended or adjusted under 35 U.S.C. 154(b) by 272 days.

(21) Appl. No.: 16/922,898

(22) Filed: Jul. 7, 2020

(65) Prior Publication Data

US 2021/0011094 A1 Jan. 14, 2021

Related U.S. Application Data

(60) Provisional application No. 62/926,043, filed on Oct. 25, 2019, provisional application No. 62/873,694, filed on Jul. 12, 2019.

(51) Int. Cl.
*G01R 33/00* (2006.01)
*A61B 5/00* (2006.01)
*A61B 5/245* (2021.01)

(52) U.S. Cl.
CPC .......... *G01R 33/0017* (2013.01); *A61B 5/245* (2021.01); *A61B 5/6814* (2013.01); *A61B 2560/0223* (2013.01)

(58) Field of Classification Search
CPC .... G01R 33/0017; A61B 5/245; A61B 5/6814
See application file for complete search history.

(56) References Cited

U.S. PATENT DOCUMENTS

| | | |
|---|---|---|
| 3,173,082 A | 3/1965 | Bell et al. |
| 3,257,608 A | 6/1966 | Bell et al. |

(Continued)

FOREIGN PATENT DOCUMENTS

| | | |
|---|---|---|
| CN | 104730484 | 6/2015 |
| CN | 107562188 | 1/2018 |

(Continued)

OTHER PUBLICATIONS

Okada, Y.C., Lahteenmäki, A. and Xu, C., "Experimental analysis of distortion of magnetoencephalography signals by the skull." Clinical neurophysiology 110 (2), 230-238 (1999).

(Continued)

*Primary Examiner* — Alvaro E Fortich
(74) *Attorney, Agent, or Firm* — Branch Partners PLLC; Bruce E. Black

(57) ABSTRACT

A calibration arrangement of a magnetic field measurement device includes at least one attachment point nub configured for attachment to the magnetic field measurement device; mounting arms extending from the at least one attachment point nub; and reference coil loops distributed among the mounting arms. A magnetic field measurement system includes the calibration arrangement and a magnetic field measurement device including a sensor mounting body, magnetic field sensors disposed on or within the sensor mounting body, and at least one primary attachment point formed in or on the sensor mounting body configured to receive the at least one attachment point nub of the calibration arrangement.

20 Claims, 6 Drawing Sheets

(56) References Cited

U.S. PATENT DOCUMENTS

| | | |
|---|---|---|
| 3,495,161 A | 2/1970 | Bell |
| 3,501,689 A | 3/1970 | Robbiano |
| 3,513,381 A | 5/1970 | Happer, Jr. |
| 4,193,029 A | 3/1980 | Cioccio et al. |
| 4,951,674 A | 8/1990 | Zanakis et al. |
| 5,189,368 A | 2/1993 | Chase |
| 5,192,921 A | 3/1993 | Chantry et al. |
| 5,225,778 A | 7/1993 | Chaillout et al. |
| 5,254,947 A | 10/1993 | Chaillout et al. |
| 5,309,095 A | 5/1994 | Ahonen et al. |
| 5,442,289 A | 8/1995 | Dilorio et al. |
| 5,444,372 A | 8/1995 | Wikswo, Jr. et al. |
| 5,471,985 A | 12/1995 | Warden |
| 5,506,200 A | 4/1996 | Hirschkoff et al. |
| 5,526,811 A | 6/1996 | Lypchuk |
| 5,713,354 A | 2/1998 | Warden |
| 6,144,872 A | 11/2000 | Graetz |
| 6,339,328 B1 | 1/2002 | Keene et al. |
| 6,472,869 B1 | 10/2002 | Upschulte et al. |
| 6,665,553 B2 | 12/2003 | Kandori et al. |
| 6,806,784 B2 | 10/2004 | Hollberg et al. |
| 6,831,522 B2 | 12/2004 | Kitching et al. |
| 7,038,450 B2 | 5/2006 | Romalis et al. |
| 7,102,451 B2 | 9/2006 | Happer et al. |
| 7,145,333 B2 | 12/2006 | Romalis et al. |
| 7,521,928 B2 | 4/2009 | Romalis et al. |
| 7,656,154 B2 | 2/2010 | Kawabata et al. |
| 7,826,065 B1 | 11/2010 | Okandan et al. |
| 7,872,473 B2 | 1/2011 | Kitching et al. |
| 7,994,783 B2 | 8/2011 | Ledbetter et al. |
| 8,054,074 B2 | 11/2011 | Ichihara et al. |
| 8,212,556 B1 | 7/2012 | Schwindt et al. |
| 8,258,884 B2 | 9/2012 | Borwick, III et al. |
| 8,319,156 B2 | 11/2012 | Borwick, III et al. |
| 8,334,690 B2 | 12/2012 | Kitching et al. |
| 8,373,413 B2 | 2/2013 | Sugioka |
| 8,405,389 B2 | 3/2013 | Sugioka et al. |
| 8,587,304 B2 | 11/2013 | Budker et al. |
| 8,836,327 B2 | 9/2014 | French et al. |
| 8,906,470 B2 | 12/2014 | Overstolz et al. |
| 8,941,377 B2 | 1/2015 | Mizutani et al. |
| 9,084,549 B2 | 7/2015 | Desain et al. |
| 9,095,266 B1 | 8/2015 | Fu |
| 9,116,201 B2 | 8/2015 | Shah et al. |
| 9,140,590 B2 | 9/2015 | Waters et al. |
| 9,140,657 B2 | 9/2015 | Ledbetter et al. |
| 9,169,974 B2 | 10/2015 | Parsa et al. |
| 9,244,137 B2 | 1/2016 | Kobayashi et al. |
| 9,291,508 B1 | 3/2016 | Biedermann et al. |
| 9,343,447 B2 | 3/2016 | Parsa et al. |
| 9,366,735 B2 | 6/2016 | Kawabata et al. |
| 9,383,419 B2 | 7/2016 | Mizutani et al. |
| 9,395,425 B2 | 7/2016 | Diamond et al. |
| 9,417,293 B2 | 8/2016 | Schaffer et al. |
| 9,429,918 B2 | 8/2016 | Parsa et al. |
| 9,568,565 B2 | 2/2017 | Parsa et al. |
| 9,575,144 B2 | 2/2017 | Komack et al. |
| 9,601,225 B2 | 3/2017 | Parsa et al. |
| 9,638,768 B2 | 5/2017 | Foley et al. |
| 9,639,062 B2 | 5/2017 | Dyer et al. |
| 9,677,905 B2 | 6/2017 | Waters et al. |
| 9,726,626 B2 | 8/2017 | Smith et al. |
| 9,726,733 B2 | 8/2017 | Smith et al. |
| 9,791,536 B1 * | 10/2017 | Alem ............... G01R 33/032 |
| 9,829,544 B2 | 11/2017 | Bulatowicz |
| 9,846,054 B2 | 12/2017 | Waters et al. |
| 9,851,418 B2 | 12/2017 | Wolf et al. |
| 9,869,731 B1 | 1/2018 | Hovde et al. |
| 9,915,711 B2 | 3/2018 | Komack et al. |
| 9,927,501 B2 | 3/2018 | Kim et al. |
| 9,948,314 B2 | 4/2018 | Dyer et al. |
| 9,964,609 B2 | 5/2018 | Ichihara et al. |
| 9,964,610 B2 | 5/2018 | Shah et al. |
| 9,970,999 B2 | 5/2018 | Larsen et al. |
| 9,995,800 B1 | 6/2018 | Schwindt et al. |
| 10,024,929 B2 | 7/2018 | Parsa et al. |
| 10,088,535 B1 | 10/2018 | Shah |
| 10,162,016 B2 | 12/2018 | Gabrys et al. |
| 10,194,865 B2 | 2/2019 | Le et al. |
| 10,314,508 B2 | 6/2019 | Desain et al. |
| 10,371,764 B2 | 8/2019 | Morales et al. |
| 10,772,561 B2 | 9/2020 | Donaldson |
| 2004/0232912 A1 | 11/2004 | Tsukamoto et al. |
| 2005/0007118 A1 | 1/2005 | Kitching et al. |
| 2005/0046851 A1 | 3/2005 | Riley, Jr. et al. |
| 2005/0206377 A1 | 9/2005 | Romalis et al. |
| 2006/0095220 A1 * | 5/2006 | Vrba ..................... A61B 5/245 |
| | | 702/104 |
| 2007/0076776 A1 | 4/2007 | Lust et al. |
| 2007/0120563 A1 | 5/2007 | Kawabata et al. |
| 2007/0167723 A1 | 7/2007 | Park et al. |
| 2007/0205767 A1 | 9/2007 | Xu et al. |
| 2009/0054758 A1 * | 2/2009 | Dunseath ................ A61B 5/05 |
| | | 600/421 |
| 2009/0079426 A1 | 3/2009 | Anderson |
| 2009/0101806 A1 | 4/2009 | Masuda |
| 2010/0219820 A1 | 9/2010 | Skidmore et al. |
| 2011/0062956 A1 | 3/2011 | Edelstein et al. |
| 2012/0112749 A1 | 5/2012 | Budker et al. |
| 2013/0082700 A1 | 4/2013 | Mizutani et al. |
| 2013/0082701 A1 | 4/2013 | Mizutani et al. |
| 2013/0265042 A1 | 10/2013 | Kawabata et al. |
| 2014/0121491 A1 | 5/2014 | Zhang |
| 2014/0306700 A1 | 10/2014 | Kamada et al. |
| 2014/0354275 A1 | 12/2014 | Sheng et al. |
| 2015/0022200 A1 | 1/2015 | Ichihara et al. |
| 2015/0054504 A1 | 2/2015 | Ichihara et al. |
| 2015/0304048 A1 * | 10/2015 | Kim .................... H04Q 11/0005 |
| | | 398/208 |
| 2015/0378316 A1 | 12/2015 | Parsa et al. |
| 2016/0061913 A1 | 3/2016 | Kobayashi et al. |
| 2016/0116553 A1 * | 4/2016 | Kim ..................... G01R 33/032 |
| | | 324/304 |
| 2016/0223627 A1 | 8/2016 | Shah et al. |
| 2016/0291099 A1 | 10/2016 | Ueno |
| 2016/0313417 A1 | 10/2016 | Kawabata et al. |
| 2017/0023653 A1 | 1/2017 | Kobayashi et al. |
| 2017/0023654 A1 | 1/2017 | Kobayashi et al. |
| 2017/0067969 A1 | 3/2017 | Butters et al. |
| 2017/0199138 A1 | 7/2017 | Parsa et al. |
| 2017/0199251 A1 | 7/2017 | Fujii et al. |
| 2017/0261564 A1 | 9/2017 | Gabrys et al. |
| 2017/0331485 A1 | 11/2017 | Gobet et al. |
| 2017/0343617 A1 | 11/2017 | Manickam et al. |
| 2017/0343695 A1 | 11/2017 | Stetson et al. |
| 2017/0356969 A1 | 12/2017 | Ueno |
| 2017/0360322 A1 | 12/2017 | Ueno |
| 2017/0363695 A1 | 12/2017 | Ueno |
| 2018/0003777 A1 | 1/2018 | Sorenson et al. |
| 2018/0038921 A1 | 2/2018 | Parsa et al. |
| 2018/0100749 A1 | 4/2018 | Waters et al. |
| 2018/0128885 A1 | 5/2018 | Parsa et al. |
| 2018/0156875 A1 | 6/2018 | Herbsommer et al. |
| 2018/0219353 A1 | 8/2018 | Shah |
| 2018/0238974 A1 | 8/2018 | Shah et al. |
| 2018/0313908 A1 | 11/2018 | Knappe et al. |
| 2018/0313913 A1 | 11/2018 | DeNatale et al. |
| 2018/0372813 A1 | 12/2018 | Bulatowicz et al. |
| 2019/0391213 A1 | 12/2019 | Alford |
| 2020/0025844 A1 | 1/2020 | Alford et al. |
| 2020/0057115 A1 | 2/2020 | Jimenez-Martinez et al. |
| 2020/0057116 A1 | 2/2020 | Zorzos et al. |
| 2020/0064421 A1 | 2/2020 | Kobayashi et al. |
| 2020/0072916 A1 | 3/2020 | Alford et al. |
| 2020/0088811 A1 | 3/2020 | Mohseni |
| 2020/0241094 A1 | 7/2020 | Alford |
| 2020/0256929 A1 | 8/2020 | Ledbetter et al. |
| 2020/0309873 A1 | 10/2020 | Ledbetter et al. |
| 2020/0334559 A1 | 10/2020 | Anderson et al. |
| 2020/0341081 A1 | 10/2020 | Mohseni et al. |
| 2020/0381128 A1 | 12/2020 | Pratt et al. |
| 2020/0400763 A1 | 12/2020 | Pratt |

(56) References Cited

U.S. PATENT DOCUMENTS

| | | |
|---|---|---|
| 2021/0015427 A1 | 1/2021 | Shah et al. |
| 2021/0063510 A1 | 3/2021 | Ledbetter |

FOREIGN PATENT DOCUMENTS

| | | |
|---|---|---|
| CN | 110742607 | 2/2020 |
| CN | 110859610 | 3/2020 |
| EP | 2738627 A3 | 6/2014 |
| EP | 2380029 B1 | 10/2015 |
| EP | 3037836 B1 | 9/2017 |
| JP | 2016109665 | 6/2016 |
| JP | 2018004462 | 1/2018 |
| WO | 2005/081794 | 9/2005 |
| WO | 2014/031985 | 2/2014 |
| WO | 2017/095998 | 6/2017 |
| WO | 2020/084194 | 4/2020 |

OTHER PUBLICATIONS

Robinson, J.T., Pohlmeyer, E., Gather, M.C., Kemere, C., Kitching, J.E., Malliaras, G.G., Marblestone, A., Shepard, K.L., Stieglitz, T. and Xie, C., "Developing Next-Generation Brain Sensing Technologies—A Review." IEEE sensors journal, 19(22), 10163-10175 (2019).

Shah, V., Knappe, S., Schwindt, P.D. and Kitching, J., "Subpicotesla atomic magnetometry with a microfabricated vapour cell." Nature Photon 1, 649-652 (2007).

Griffith, W.C., Knappe, S. and Kitching, J., "Femtotesla atomic magnetometry in a microfabricated vapor cell." Optics express 18, (26), 27167-27172 (2010).

Tierney, T.M., Holmes, N., Mellor, S., López, J.D., Roberts, G., Hill, R.M., Boto, E., Leggett, J., Shah, V., Brookes, M.J. and Bowtell, R., "Optically pumped magnetometers: From quantum origins to multichannel magnetoencephalography." NeuroImage, 199, 598-608 (2019).

Iivanainen, J., Zetter, R., Grön, M., Hakkarainen, K. and Parkkonen, L., "On-scalp MEG system utilizing an actively shielded array of optically-pumped magnetometers." Neuroimage 194, 244-258 (2019).

Iivanainen, J., Stenroos, M. and Parkkonen, L., "Measuring MEG closer to the brain: Performance of on-scalp sensor arrays." NeuroImage 147, 542-553 (2017).

Kitching, J., Knappe, S., Gerginov, V., Shah, V., Schwindt, P.D., Lindseth, B., Donley E.A., "Chip-scale atomic devices precision atomic instruments based on MEMS." In Frequency Standards and Metrology, 445-453 (2009).

Kitching, J., Knappe, S. and Donley, E.A., "Atomic sensors—a review." IEEE Sensors Journal, 11(9), 1749-1758 (2011).

Budker, D. and Romalis, M., "Optical magnetometry". Nature physics, 3(4), 227-234 (2007).

Happer, W., "Optical pumping", Rev. Mod. Phys., 44 (2), 169-249 (1972).

Purcell, E.M., Field, G.B., "Influence of collisions upon population of hyperfine states in hydrogen", Astrophys. J., 124, 542 (1956).

Ledbetter, M.P., Savukov, I.M., Acosta, V.M., Budker, D. and Romalis, M.V., "Spin-exchange-relaxation-free magnetometry with Cs vapor." Physical Review A, 77(3), 033408 (2008).

Bloom, A. L., "Principles of operation of the rubidium vapor magnetometer." Applied Optics 1(1), 61-68 (1962).

Bell, W.E., and Bloom, A.L., "Optically driven spin precession." Physical Review Letters 6, (6), 280 (1961).

Roberts, G., Holmes, N., Alexander, N., Boto, E., Leggett, J., Hill, R.M., Shah, V., Rea, M., Vaughan, R., Maguire, E.A. and Kessler, K., "Towards OPM-MEG in a virtual reality environment." NeuroImage, 199, 408-417 (2019).

Zhang, R., Xiao, W., Ding, Y., Feng, Y., Peng, X., Shen, L., Sun, C., Wu, T., Wu, Y., Yang, Y. and Zheng, Z., "Recording brain activities in unshielded Earth's field with optically pumped atomic magnetometers." Science Advances, 6(24) (2020).

De Cheveigné, A., Wong, D.D., Di Liberto, G.M., Hjortkjaer, J., Slaney, M. and Lalor, E., "Decoding the auditory brain with canonical component analysis." NeuroImage, 172, 206-216 (2018).

Mellinger, J., Schalk, G., Braun, C., Preissl, H., Rosenstiel, W., Birbaumer, N. and Kübler, A., "An MEG-based brain-computer interface (BCI)." Neuroimage, 36(3), 581-593 (2007).

Wolpaw, J.R. McFarland, D.J., Neat, G.W. and Forneris, C.A., "An EEG-based brain-computer interface for cursor control." Electroencephalography and clinical neurophysiology, 78(3), 252-259 (1991).

Lightfoot, G., "Summary of the N1-P2 cortical auditory evoked potential to estimate the auditory threshold in adults". Seminars in hearing, 37(1), 1 (2016).

Virtanen, J., Ahveninen, J., Iilmoniemi, R. J., Näätänen, R., & Pekkonen, E., "Replicability of MEG and EEG measures of the auditory N1/N1m-response." Electroencephalography and Clinical Neurophysiology/Evoked Potentials Section, 108(3), 291-298(1998).

Gascoyne, L., Furlong, P. L., Hillebrand, A., Worthen, S. F., & Witton, C., "Localising the auditory N1m with event-related beamformers: localisation accuracy following bilateral and unilateral stimulation." Scientific reports, 6(1), 1-9 (2016).

Borna, A., Carter, T.R., Goldberg, J.D., Colombo, A.P., Jau, Y.Y., Berry, C., McKay, J., Stephen, J., Weisend, M. and Schwindt, P.D., "A 20-channel magnetoencephalography system based on optically pumped magnetometers." Physics in Medicine & Biology, 62(23), 8909 (2017).

Pyragius, T., Marin Florez, H., & Fernholz, T. (2019). A Voigt effect based 3D vector magnetometer. Physical Review A, 100(2), https://doi.org/10.1103/PhysRevA.100.023416.

Rui Zhang, Rahul Mhaskar, Ken Smith, Easswar Balasubramaniam, Mark Prouty. "All Optical Scalar Atomic Magnetometer Capable of Vector Measurement," Submitted on Nov. 17, 2020. https://arxiv.org/abs/2011.08943; Geometries, Inc., San Jose, CA, 95131, USA.

Alled, J. C., Lyman, R. N., Kornack, T. W., & Romalis, M. V. (2002). High-sensitivity atomic magnetometer unaffected by spin-exchange relaxation. Physical review letters, 89(13), 130801.

Balabas et al. Polarized alkali vapor with minute-long transverse spin-relaxation time, Phys. Rev. Lett 105, 070801—Published Aug. 12, 2010.

Barbieri, F., Trauchessec, V., Caruso, L., Trejo-Rosillo, J., Telenczuk, B., Paul, E., . . . & Ouanounou, G. (2016). Local recording of biological magnetic fields using Giant Magneto Resistance-based micro-probes. Scientific reports, 6, 39330.

Dmitry Budker and Michael Romalis, "Optical Magnetometry," Nature Physics, 2008, https://arxiv.org/abs/physics/0611246v1.

Anthony P. Colombo, Tony R. Carter, Amir Borna, Yuan-Yu Jau, Cort N. Johnson, Amber L. Dagel, and Peter D. D. Schwindt, "Four-channel optically pumped atomic magnetometer for magnetoencephalography," Opt. Express 24, 15403-15416 (2016).

Dang, H.B. & Maloof, A.C. & Romalis, Michael (2009). Ultra-high sensitivity magnetic field and magnetization measurements with an atomic magnetometer. Applied Physics Letters. 97. 10.1063/1.3491215.

Donley, E.A. & Hodby, E & Hollberg, L & Kitching, J. (2007). Demonstration of high-performance compact magnetic shields for chip-scale atomic devices. The Review of scientific instruments. 78. 083102.

Hämäläinen, Matti & Hari, Riitta & Ilmoniemi, Risto J. & Knuutila, Jukka & Lounasmaa, Olli V. Apr. 1993. Magnetoencephalograph—theory, instrumentation, and applications to noninvasive studies of the working human brain. Reviews of Modern Physics. vol. 65, Issue 2. 413-497.

Hunter, D. and Piccolomo, S. and Pritchard, J. D. and Brockie, N. L. and Dyer, T. E. and Riis, E. (2018) Free-induction-decay magnetometer based on a microfabricated Cs vapor cell Physical Review Applied (10).ISSN 2331-7019.

Jiménez-Martinez, R., Griffilh, W. C., Wang, Y. J., Knappe, S., Kitching, J., Smith, K., & Prouty, M. D. (2010). Sensitivity comparison of Mx and frequency-modulated bell-bloom Cs magnetometers in a microfabricated cell. IEEE Transactions on Instrumentation and Measurement, 59(2), 372-378.

Kiwoong Kim, Sarno Begus, Hui Xia, Seung-Kyun Lee, Vojko Jazbinsek, Zvonko Trontelj, Michael V. Romalis, Multi-channel

(56) References Cited

OTHER PUBLICATIONS atomic magnetometer for magnetoencephalography: A configuration study. NeuroImage 89 (2014) 143-151 http://physics.princeton.edu/romalis/papers/Kim_2014.pdf.

Knappe, Svenja & Sander, Tilmann & Trahms, Lutz. (2012). Optically-Pumped Magnetometers for MEG. Magnetoencephalography: From Signals to Dynamic Cortical Networks. 993-999. 10.1007/978-3-642-33045-2_49.

Kominis, I.K., Kornack, T.W., Allred, J.C. and Romalis, M.V., 2003. A subfemtotesla multichannel atomic magnetometer. Nature, 422(6932), p. 596.

Korth, H., K. Strohbehn, F. Tejada, A. G. Andreou, J. Kitching, S. Knappe, S. J. Lehtonen, S. M. London, and M. Kafel (2016), Miniature atomic scalarmagnetometer for space based on the rubidium isotope 87Rb, J. Geophys. Res. Space Physics, 121, 7870-7880, doi: 10.1002/2016JA022389.

Lenz, J. and Edelstein, S., 2006. Magnetic sensors and their applications. IEEE Sensors journal, 6(3), pp. 631-649.

Li, S & Vachaspati, Pranjal & Sheng, Dehong & Dural, Nezih & Romalis, Michael. (2011). Optical rotation in excess of 100 rad generated by Rb vapor in a multipass cell. Phys. Rev. A. 84. 10.1103/PhysRevA.84.061403.

Maze, J. R., Stanwix, P. L., Hodges, J. S., Hong, S., Taylor, J. M., Cappellaro, P., . . . & Yacoby, A. (2008). Nanoscale magnetic sensing with an individual electronic spin in diamond. Nature, 455(7213), 644.

Sander TH, Preusser J, Mhaskar R, Kitching J, Trahms L, Knappe S. Magnetoencephalography with a chip-scale atomic magnetometer Biomed Opt Express. 2012;3(5):981-90.

J. Seltzer, S & Romalis, Michael. (2010). High-temperature alkali vapor cells with antirelaxation surface coatings. Journal of Applied Physics. 106. 114905-114905. 10.1063/1.3236649.

Seltzer, S. J., and Romalis, M.V., "Unshielded three-axis vector operation of a spin-exchange-relaxation-free atomic magnetometer." Applied physics letters 85.20 (2004): 4804-4806.

Sheng, Dong & R. Perry, Abigail & Krzyzewski, Sean & Geller, Shawn & Kitching, John & Knappe, Svenja. (2017). A microfabricated optically-pumped magnetic gradiometer. Applied Physics Letters. 110. 10.1063/1.4974349.

Sheng, Dehong & Li, S & Dural, Nezih & Romalis, Michael. (2013). Subfemtotesla Scalar Atomic Magnetometry Using Multipass Cells. Physical review letters. 110. 160802. 10.1103/PhysRevLett.110.160802.

Volkmar Schultze et al. An Optically Pumped Magnetometer Working in the Light-Shift Dispersed Mz Mode, Sensors 2017, 17, 561; doi:10.3390/s17030561.

Fang, J. and Qin, J., 2012. In situ triaxial magnetic field compensation for the spin-exchange-relaxation-free atomic magnetometer. Review of Scientific Instruments, 83(10), p. 103104.

Joon Lee, Hyun & Shim, Jeong & Moon, Han Seb & Kim, Kiwoong. (2014). Flat-response spin-exchange relaxation free atomic magnetometer under negative feedback Optics Express. 22. 10.1364/OE.22.019887.

Griflith, Clark & Jimenez-Martinez, Ricardo & Shah, Vishal & Knappe, Svenja & Kitching, John. (2009). Miniature atomic magnetometer integrated with flux concentrators. Applied Physics Letters—Appl Phys Lett.94. 10.1063/1.3056152.

Lee, S.-K & Romalis, Michael. (2008). Calculation of Magnetic Field Noise from High-Permeability Magnetic Shields and Conducting Objects with Simple Geometry. Journal of Applied Physics. 103. 084904-084904. 10.1063/1.2885711.

Vovrosh, Jamie & Voulazeris, Georgios & Petrov, Plamen & Zou, Ji & Gaber Beshay, Youssef & Benn, Laura & Woolger, David & Attallah, Moataz & Boyer, Vincent & Bongs, Kai & Holynski, Michael. (2018). Additive manufacturing of magnetic shielding and ultra-high vacuum flange for cold atom sensors. Scientific Reports. 8. 10.1038/s41598-018-20352-x.

Kim, Young Jin & Savukov, I. (2016). Ultra-sensitive Magnetic Microscopy with an Optically Pumped Magnetometer. Scientific Reports 6. 24773. 10.1038/srep24773.

Navau, Carles & Prat-Camps, Jordi & Sanchez, Alvaro. (2012). Magnetic Energy Harvesting and Concentration at a Distance by Transformation Optics. Physical review letters. 109. 263903. 10.1103/PhysRevLett.109.263903.

Orang Alem, Rahul Mhaskar, Ricardo Jiménez-Martinez, Dong Sheng, John LeBlanc, Lutz Trahms, Tilmann Sander, John Kitching, and Svenja Knappe, "Magnetic field imaging with microfabricated optically-pumped magnetometers," Opt. Express 25, 7849-7858 (2017).

Slocum et al., Self-Calibrating Vector Magnetometer for Space, https://esto.nasa.gov/conferences/estc-2002/Papers/B3P4(Slocum).pdf.

Dupont-Roc, J & Haroche, S & Cohen-Tannoudji, C. (1969). Detection of very weak magnetic fields (10-9gauss) by 87Rb zero-field level crossing resonances. Physics Letters A—Phys Lett A. 28. 638-639. 10.1016/0375-9601(69) 90480-0.

J. A. Neuman, P. Wang, and A. Gallagher, Robust high-temperature sapphire cell for metal vapors, Review of Scientific Instruments, vol. 66, Issue 4, Apr. 1995, pp. 3021-3023.

Borna, Amir, et al. "A 20-channel magnetoencephalography system based on optically pumped magnetometers." Physics in Medicine & Biology 62.23 (2017): 8909.

R. E. Slocum & L. J. Ryan, Design and operation of the minature vector laser magnetometer, Nasa Earth Science Technology Conference 2003.

Schoenmaker, Jeroen & R Pirota, K & Teixeira, Julio. (2013). Magnetic flux amplification by Lenz lenses. The Review of scientific instruments. 84. 085120. 10.1063/1.4819234.

Hu, Yanhui & Hu, Zhaohui & Liu, Xuejing & Li, Yang & Zhang, Ji & Yao, Han & Ding, Ming. (2017). Reduction of far off-resonance laser frequency drifts based on the second harmonic of electro-optic modulator detection in the optically pumped magnetometer. Applied Optics. 56. 5927. 10.1364/AO.56.005927.

Masuda, Y & Ino, T & Skoy, Vadim & Jones, G.L. (2005). 3He polarization via optical pumping in a birefringent cell. Applied Physics Letters. 87. 10.1063/1.2008370.

A.B. Baranga et al., An atomic magnetometer for brain activity imaging, Real Time Conference 2005. 14th IEEE-NPSS. pp. 417-418.

Larry J. Ryan, Robert E. Slocum, and Robert B. Steves, Miniature Vector Laser Magnetometer Measurements of Earth's Field, May 10, 2004, 4 pgs.

Lorenz, V. O., Dai, X., Green, H., Asnicar, T. R., & Cundiff, S. T. (2008). High-density, high-temperature alkali vapor cell. Review of Scientific Instruments, 79(12), 4 pages.

F. Jackson Kimball, D & Dudley, J & Li, Y & Thulasi, Swecha & Pustelny, Szymon & Budker, Dmitry & Zolotorev, Max. (2016). Magnetic shielding and exotic spin-dependent interactions. Physical Review D. 94. 10.1103/PhysRevD.94.082005.

Huang, Haichao, et al. "Single-beam three-axis atomic magnetometer." Applied Physics Letters 109.6 (2016): 062404. (Year: 2016).

Scott Jeffrey Seltzer: "Developments in alkali-metal atomic magnetometry", Nov. 1, 2008 (Nov. 1, 2008), XP055616618, ISBN: 978-0-549-93355-7 Retrieved from the Internet: URL:http://physics.princeton.edu/atomic/romalis/papers/Seltzer%20Thesis.pdf [retrieved on Aug. 29, 2019] pp. 148-159.

Haifeng Dong et al: "Atomic-Signal-Based Zero-Field Finding Technique for Unshielded Atomic Vector Magnetometer", IEEE Sensors Journal, IEEE Service Center, New York, NY, US, vol. 13, No. 1, Jan. 1, 2013 (Jan. 1, 2013), pp. 186-189.

Boto, E, Holmes, N, Leggett, J, Roberts, G, Shah, V, Meyer, SS, Muñoz, LD, Mullinger, KJ, Tierney, TM, Bestmann, S, Barnes, GR, Bowtell, R & Brookes, MJ 2018, 'Moving magnetoencephalography towards real world applications with a wearable system', Nature, vol. 555, pp. 657-661.

Ijsselsteijn, R & Kielpinski, Mark & Woetzel, S & Scholtes, Theo & Kessler, Ernst & Stolz, Ronny & Schultze, V & Meyer, H-G. (2012). A full optically operated magnetometer array: An experimental study. The Review of scientific instruments. 83. 113106. 10.1063/1.4766961.

Tierney, T. M., Holmes, N., Meyer, S. S., Boto, E., Roberts, G., Leggett, J., . . . Barnes, G. R. (2018). Cognitive neuroscience using

(56) References Cited

OTHER PUBLICATIONS wearable magnetometer arrays: Non-invasive assessment of language function. NeuroImage, 181, 513-520.
Manon Kok, Jeroen D. Hol and Thomas B. Schon (2017), "Using Inertial Sensors for Position and Orientation Estimation", Foundations and Trends in Signal Processing: vol. 11: No. 1-2, pp. 1-153. http://dx.doi.org/10.1561/2000000094.
Zhang Xin et al: "Detection and analysis of MEG signals in occipital region with double-channel OPM sensors", Journal of Neuroscience Methods, Elsevier Science Publisher B. V., Amsterdam, NL, vol. 346, Sep. 17, 2020 (Sep. 17, 2020).
Hill RM, Boto E, Holmes N, et al. A tool for functional brain imaging with lifespan compliance [published correction appears in NatCommun. Dec. 4, 2019;10(1):5628]. NatCommun. 2019;10(1):4785. Published Nov. 5, 2019. doi:10.1038/S41467-019-12486-x.
Zetter, R., Iivanainen, J & Parkkonen, L. Optical Co-registration of MRI and On-scalp MEG Sci Rep 9, 5490 (2019) https://doi.org/10.1038/s41598-019-41763-4.
Garrido-Jurado, Sergio, Rafael Muñoz-Salinas, Francisco José Madrid-Cuevas and Manuel J. Marín-Jiménez. "Automatic generation and detection of highly reliable fiducial markers under occlusion." Pattern Recognit. 47 (2014): 2280-2292.
Hill RM, Boto E, Rea M, et al. Multi-channel whole-head OPM-MEG: Helmet design and a comparison with a conventional system [published online ahead of print, May 29, 2020]. Neuroimage. 2020;219:116995. doi: 10.1016/j.neuroimage.2020.116995.
V. Kazemi and J. Sullivan, "One millisecond face alignment with an ensemble of regression trees," 2014 IEEE Conference on Computer Vision and Pattern Recognition, Columbus, OH, 2014, pp. 1867-1874, doi: 10.1109/CVPR.2014.241.
Holmes, N., Tierney, T.M., Leggett, J. et al. Balanced, bi-planar magnetic field and field gradient coils for field compensation in wearable magnetoencephalography. Sci Rep 9, 14196 (2019).
N. Holmes, J. Leggett, E. Boto, G. Roberts, R.M. Hill, T.M. Tierney, V. Shah, G.R. Barnes, M.J. Brookes, R. Bowtell A bi-planar coil system for nulling background magnetic fields in scalp mounted magnetoencephalography Neuroimage, 181 (2018), pp. 760-774.
J. M. Leger et al., In-flight performance of the Absolute Scalar Magnetometer vector mode on board the Swarm satellites, Earth, Planets, and Space (2015) 67:57.
Alexandrov, E. B., Balabas, M. V., Kulyasov, V. N., Ivanov, A. E., Pazgalev, A. S., Rasson, J. L., . . . (2004). Three-component variometer based on a scalar potassium sensor. Measurement Science and Technology, 15(5), 918-922.
Gravrand, O., Khokhlov, A., & JL, L. M. (2001). On the calibration of a vectorial 4He pumped magnetometer. Earth, planets and space , 53 (10), 949-958.
Borna, Amir & Carter, Tony & Colombo, Anthony & Jau, Y-Y & McKay, Jim & Weisend, Michael & Taulu, Samu & Stephen, Julia & Schwindt, Peter. (2018). Non-Invasive Functional-Brain-Imaging with a Novel Magnetoencephalography System. 9 Pages.
Vrba J, Robinson SE. Signal processing in magnetoencephalography. Methods. 2001;25(2):249-271. doi:10.1006/meth.2001.1238.
Uusitalo M and Ilmoniemi R., 1997, Signal-space projection method for separating MEG or EEG into components Med. Biol. Comput (35) 135-140.
Taulu S and Kajola M., 2005, Presentation of electromagnetic multichannel data: the signal space separation method. J. Appl. Phys. (97) 124905 (2005).
Taulu S, Simola J and Kajola M., 2005, Applications of the signal space separation method. IEEE Trans. Signal Process. (53) 3359-3372 (2005).
Taulu S, Simola J., 2006, Spatiotemporal signal space separation method for rejecting nearby interference in MEG measurements. Phys. Med Biol. (51) 1759-1768 (2006).
Johnson, et al., Magnetoencephalography with a two-color pump-probe, fiber-coupled atomic magnetometer, Applied Physics Letters 97, 243703 2010.
Zhang, et al., Magnetoencephalography using a compact multichannel atomic magnetometer with pump-probe configuration, AIP Advances 8, 125028 (2018).
Xia, H. & Ben-Amar Baranga, Andrei & Hoffman, D. & Romalis, Michael. (2006). Magnetoencephalography with an atomic magnetometer. Applied Physics Letters—Appl Phys Lett. 89. 10.1063/1.2392722.
Ilmoniemi, R. (2009). The triangle phantom in magnetoencephalography. In 24th Annual Meeting of Japan Biomagnetism and Bioelecctromagnetics Society, Kanazawa, Japan, 28.29.5.2009 (pp. 6263).
Oyama D. Dry phantom for magnetoencephalography—Configuration, calibration, and contribution. J Neurosci Methods. 2015;251:24-36. doi: 0.1016/j.jneumeth.2015.05.004.
Chutani, R., Maurice, V., Passilly, N. et al. Laser light routing in an elongated micromachined vapor cell with diffraction gratings for atomic clock applications. Sci Rep 5, 14001 (2015). https://doi.org/10.1038/srep14001.
Eklund, E. Jesper, Andrei M. Shkel, Svenja Knappe, Elizabeth A. Donley and John Kitching. "Glass-blown spherical microcells for chip-scale atomic devices." (2008).
Jiménez-Martinez R, Kennedy DJ, Rosenbluh M, et al. Optical hyperpolarization and NMR detection of 129Xe on a microfluidic chip. Nat Commun. 2014;5:3908. Published May 20, 2014. doi:10.1038/ncomms4908.
Boto, Elena, Sofie S. Meyer, Vishal Shah, Orang Alem, Svenja Knappe, Peter Kruger, T. Mark Fromhold, et al. "A New Generation of Magnetoencephalography: Room Temperature Measurements Using Optically-Pumped Magnetometers." NeuroImage 149 (Apr. 1, 2017): 404-14.
Bruno, A. C., and P. Costa Ribeiro. "Spatial Fourier Calibration Method for Multichannel Squid Magnetometers." Review of Scientific Instruments 62, No. 4 (Apr. 1, 1991): 1005-9.
Chella, Federico, Filippo Zappasodi, Laura Marzetti, Stefania Della Penna, and Vittorio Pizzella. "Calibration of a Multichannel MEG System Based on the Signal Space Separation Method." Physics in Medicine and Biology 57 (Jul. 13, 2012): 4855-70.
Pasquarelli, A, M De Melis, Laura Marzetti, Hans-Peter Müller, and S N Erné. "Calibration of a Vector-MEG Helmet System." Neurology & Clinical Neurophysiology□: NCN 2004 (Feb. 1, 2004): 94.
Pfeiffer, Christoph, Lau M. Andersen, Daniel Lundqvist, Matti Hämäläinen, Justin F. Schneiderman, and Robert Oostenveld. "Localizing On-Scalp MEG Sensors Using an Array of Magnetic Dipole Coils." Plos One 13, No. 5 (May 10, 2018): e0191111.
Vivaldi, Valentina, Sara Sommariva, and Alberto Sorrentino. "A Simplex Method for the Calibration of a MEG Device." Communications in Applied and Industrial Mathematics 10 (Jan. 1, 2019): 35-46.
Nagel, S., & Spuler, M. (2019). Asynchronous non-invasive high-speed BCI speller with robust non-control state detection. Scientific Reports, 9(1), 8269.
Thielen, J., van den Broek, P., Farquhar, J., & Desain, P. (2015). Broad-Band Visually Evoked Potentials: Re(con)volution in Brain-Computer Interfacing. PloS One, 10(7), e0133797. https://doi.org/10.1371/journal.pone.0133797.
J. Kitching, "Chip-scale atomic devices," Appl. Phys. Rev. 5(3), 031302 (2018), 39 pages.
Arjen Stolk, Ana Todorovic, Jan-Mathijs Schoffelen, and Robert Oostenveld. "Online and offline tools for head movement compensation in MEG." Neuroimage 68 (2013): 39-48.
Bagherzadeh, Yasaman, Daniel Baldauf, Dimitrios Pantazis, and Robert Desimone. "Alpha synchrony and the neurofeedback control of spatial attention." Neuron 105, No. 3 (2020): 577-587.

* cited by examiner

DETACHABLE ARRANGEMENT FOR ON-SCALP MAGNETOENCEPHALOGRAPHY (MEG) CALIBRATION

CROSS-REFERENCE TO RELATED APPLICATIONS

This application claims the benefit of U.S. Provisional Patent Application Ser. Nos. 62/873,694, filed Jul. 12, 2019, and 62/926,043, filed Oct. 25, 2019, both of which are incorporated herein by reference in their entireties.

FIELD

The present disclosure is directed to the area of magnetic field measurement systems including systems for magnetoencephalography (MEG). The present disclosure is also directed to a calibration arrangement for calibration of a magnetic field measurement system and methods and systems using the calibration arrangement.

BACKGROUND

In the nervous system, neurons propagate signals via action potentials. These are brief electric currents which flow down the length of a neuron causing chemical transmitters to be released at a synapse. The time-varying electrical currents within an ensemble of neurons generate a magnetic field. Magnetoencephalography (MEG), the measurement of magnetic fields generated by the brain, is one method for observing these neural signals.

Existing technology for measuring MEG typically utilizes superconducting quantum interference devices (SQUIDs) or collections of discrete optically pumped magnetometers (OPMs). SQUIDs require cryogenic cooling, which is bulky, expensive, requires a lot of maintenance. These requirements preclude their application to mobile or wearable devices.

An alternative to an array of SQUIDs is an array of OPMs. For MEG and other applications, the array of OPMS may have a large number of OPM sensors that are tightly packed. Such dense arrays can produce a high resolution spatial mapping of the magnetic field, and at a very high sensitivity level. Such OPMs sensors can be used for a wide range of applications, including sensing magnetic field generated by neural activities, similar to MEG systems.

BRIEF SUMMARY

One embodiment is a calibration arrangement of a magnetic field measurement device that includes at least one attachment point nub configured for attachment to the magnetic field measurement device; a plurality of mounting arms extending from the at least one attachment point nub; and a plurality of reference coil loops distributed among the mounting arms, wherein each of the reference coil loops is attached to one of the mounting arms.

Another embodiment is a magnetic field measurement system that includes the calibration arrangement and a magnetic field measurement device including a sensor mounting body, a plurality of magnetic field sensors disposed on or within the sensor mounting body, and at least one primary attachment point formed in or on the sensor mounting body and configured to receive the at least one attachment point nub of the calibration arrangement to attach the calibration arrangement to the sensor mounting body.

In at least some embodiments, each of the mounting arms includes at least one winding nub disposed along the mounting arm with one of the reference coil loops disposed around each of the at least one winding nub. In at least some embodiments, at least two of the reference coil loops are attached to one of the mounting arms. In at least some embodiments, at least one of the mounting arms is reversibly detachable from the at least one attachment point nub.

In at least some embodiments, when attached to the magnetic field measurement system, each of the reference coil loops is no closer than 1 centimeter from any of the magnetic field sensors of the magnetic field measurement device. In at least some embodiments, when attached to the magnetic field measurement system, each of the reference coil loops is no closer than 4 centimeters from any of the magnetic field sensors of the magnetic field measurement device.

In at least some embodiments, the at least one attachment point and the at least one attachment point nub have complementary features so that, when engaged, the complementary features resist rotation or translation of the calibration arrangement relative to the sensor mounting body. In at least some embodiments, the complementary features include a notch and a corresponding protrusion.

In at least some embodiments, the calibration arrangement further includes at least one secondary attachment point nub and the sensor mounting body further includes at least one secondary attachment point configured to receive the at least one secondary attachment point nub. In at least some embodiments, the magnetic field measurement system further includes a power source and leads coupling the reference coil loops to the power source.

In at least some embodiments, the magnetic field measurement system further includes a processor coupled to the power source and configured to apply different electrical signals to at least two of the reference coil loops. In at least some embodiments, the processor is further coupled to the magnetic field sensors and configured to receive signals from the magnetic field sensors. In at least some embodiments, the processor is further configured to decompose the received signals into components from each of the at least two of the reference coil loops based on at least one characteristic of the different applied electrical signals. In at least some embodiments, the processor is further configured to determine calibration parameters using the measured magnetic fields and expected measurements based on a model of the reference coil loops.

Another embodiment is a method of calibrating a magnetic field measurement device. The method includes attaching any of the calibration arrangement described above to the magnetic field measurement device; applying electrical signals through a plurality of the reference coil loops; and in response to the applied electrical signals, measuring magnetic fields generated by the reference coil loops using one or more magnetic field sensors of the magnetic field measurement device.

In at least some embodiments, attaching the calibration arrangement includes receiving the at least one attachment point nub of the calibration arrangement in or on at least one primary attachment point of a sensor mounting body of the magnetic field measurement device.

In at least some embodiments, applying the electrical signals includes applying different electrical signals to at least two of the reference coil loops. In at least some embodiments, the method further includes decomposing the measured magnetic fields into components from each of the at least two of the reference coil loops based on at least one characteristic of the different applied electrical signals.

In at least some embodiments, the method further includes determining a calibration using the measured magnetic fields and expected measurements based on a model of the reference coil loops.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein.

DETAILED DESCRIPTION

Figure 1A:
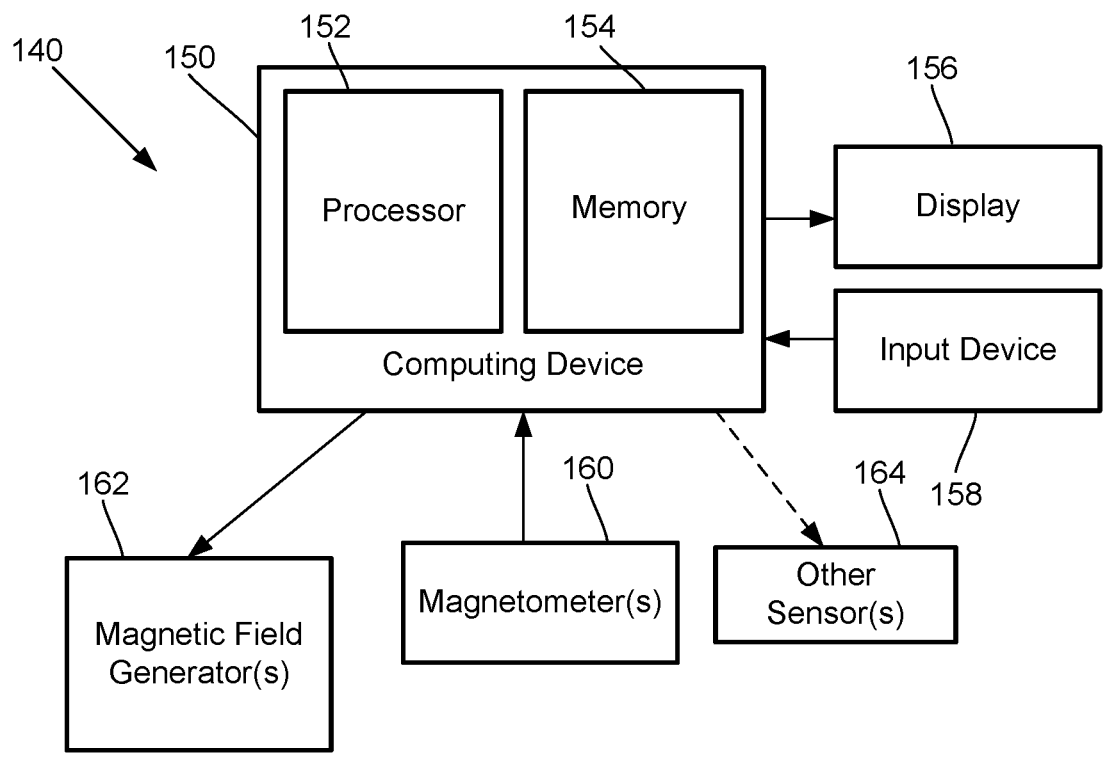
FIG. 1A is a schematic block diagram of one embodiment of a magnetic field measurement system, according to the invention.

The present disclosure is directed to the area of magnetic field measurement systems including systems for magnetoencephalography (MEG). The present disclosure is also directed to a calibration arrangement for calibration of a magnetic field measurement system and methods and systems using the calibration arrangement.

Herein the terms "ambient background magnetic field" and "background magnetic field" are interchangeable and used to identify the magnetic field or fields associated with sources other than the magnetic field measurement system and the magnetic field sources of interest, such as biological source(s) (for example, neural signals from a user's brain) or non-biological source(s) of interest. The terms can include, for example, the Earth's magnetic field, as well as magnetic fields from magnets, electromagnets, electrical devices, and other signal or field generators in the environment, except for the magnetic field generator(s) that are part of the magnetic field measurement system.

The terms "gas cell", "vapor cell", and "vapor gas cell" are used interchangeably herein. Below, a vapor cell containing alkali metal vapor is described, but it will be recognized that other vapor cells can contain different gases or vapors for operation.

The methods and systems are described herein using optically pumped magnetometers (OPMs). While there are many types of OPMs, in general magnetometers operate in two modalities: vector mode and scalar mode. In vector mode, the OPM can measure one, two, or all three vector components of the magnetic field; while in scalar mode the OPM can measure the total magnitude of the magnetic field.

Vector mode magnetometers measure a specific component of the magnetic field, such as the radial and tangential components of magnetic fields with respect the scalp of the human head. Vector mode OPMs often operate at zero-field and may utilize a spin exchange relaxation free (SERF) mode to reach femto-Tesla sensitivities. A SERF mode OPM is one example of a vector mode OPM, but other vector mode OPMs can be used at higher magnetic fields. These SERF mode magnetometers can have high sensitivity but may not function in the presence of magnetic fields higher than the linewidth of the magnetic resonance of the atoms of about 10 nT, which is much smaller than the magnetic field strength generated by the Earth.

Magnetometers operating in the scalar mode can measure the total magnitude of the magnetic field. (Magnetometers in the vector mode can also be used for magnitude measurements.) Scalar mode OPMs often have lower sensitivity than SERF mode OPMs and are capable of operating in higher magnetic field environments.

The magnetic field measurement systems, such as a MEG system, described herein can be used to measure or observe electromagnetic signals generated by one or more magnetic field sources (for example, neural signals or other biological sources) of interest. The system can measure biologically generated magnetic fields and, at least in some embodiments, can measure biologically generated magnetic fields in an unshielded or partially shielded environment. Aspects of a magnetic field measurement system will be exemplified below using magnetic signals from the brain of a user; however, biological signals from other areas of the body, as well as non-biological signals, can be measured using the system. In at least some embodiments, the system can be a wearable MEG system that can be portable and used outside a magnetically shielded room. A wearable MEG system will be used to exemplify the magnetic field measurement systems and calibration arrangements described herein; however, it will be recognized the calibration arrangements and methods described herein can be applied to other magnetic field measurement systems.

A magnetic field measurement system, such as a MEG system, can utilize one or more magnetic field sensors. Magnetometers will be used herein as an example of magnetic field sensors, but other magnetic field sensors may also be used in addition to, or as an alternative to, the magnetometers. FIG. 1A is a block diagram of components of one embodiment of a magnetic field measurement system 140 (such as a biological signal detection system.) The system 140 can include a computing device 150 or any other similar device that includes a processor 152, a memory 154, a display 156, an input device 158, one or more magnetometers 160 (for example, an array of magnetometers) which can be OPMs, one or more magnetic field generators 162, and, optionally, one or more other sensors 164 (e.g., non-magnetic field sensors). The system 140 and its use and operation will be described herein with respect to the measurement of neural signals arising from one or more magnetic field sources of interest in the brain of a user as an example. It will be understood, however, that the system can be adapted and used to measure signals from other magnetic field sources of interest including, but not limited to, other neural signals, other biological signals, as well as non-biological signals.

The computing device 150 can be a computer, tablet, mobile device, field programmable gate array (FPGA), microcontroller, or any other suitable device for processing information or instructions. The computing device 150 can be local to the user or can include components that are non-local to the user including one or both of the processor 152 or memory 154 (or portions thereof). For example, in at least some embodiments, the user may operate a terminal that is connected to a non-local computing device. In other embodiments, the memory 154 can be non-local to the user.

The computing device 150 can utilize any suitable processor 152 including one or more hardware processors that may be local to the user or non-local to the user or other components of the computing device. The processor 152 is configured to execute instructions stored in the memory 154.

Any suitable memory 154 can be used for the computing device 150. The memory 154 illustrates a type of computer-readable media, namely computer-readable storage media. Computer-readable storage media may include, but is not limited to, volatile, nonvolatile, non-transitory, removable, and non-removable media implemented in any method or technology for storage of information, such as computer readable instructions, data structures, program modules, or other data. Examples of computer-readable storage media include RAM, ROM, EEPROM, flash memory, or other memory technology, CD-ROM, digital versatile disks ("DVD") or other optical storage, magnetic cassettes, magnetic tape, magnetic disk storage or other magnetic storage devices, or any other medium which can be used to store the desired information and which can be accessed by a computing device.

Communication methods provide another type of computer readable media; namely communication media. Communication media typically embodies computer-readable instructions, data structures, program modules, or other data in a modulated data signal such as a carrier wave, data signal, or other transport mechanism and include any information delivery media. The terms "modulated data signal," and "carrier-wave signal" includes a signal that has one or more of its characteristics set or changed in such a manner as to encode information, instructions, data, and the like, in the signal. By way of example, communication media includes wired media such as twisted pair, coaxial cable, fiber optics, wave guides, and other wired media and wireless media such as acoustic, RF, infrared, and other wireless media.

The display 156 can be any suitable display device, such as a monitor, screen, or the like, and can include a printer. In some embodiments, the display is optional. In some embodiments, the display 156 may be integrated into a single unit with the computing device 150, such as a tablet, smart phone, or smart watch. In at least some embodiments, the display is not local to the user. The input device 158 can be, for example, a keyboard, mouse, touch screen, track ball, joystick, voice recognition system, or any combination thereof, or the like. In at least some embodiments, the input device is not local to the user.

The magnetic field generator(s) 162 can be, for example, Helmholtz coils, solenoid coils, planar coils, saddle coils, electromagnets, permanent magnets, or any other suitable arrangement for generating a magnetic field. As an example, the magnetic field generator 162 can include three orthogonal sets of coils to generate magnetic fields along three orthogonal axes. Other coil arrangements can also be used. The optional sensor(s) 164 can include, but are not limited to, one or more position sensors, orientation sensors, accelerometers, image recorders, or the like or any combination thereof.

The one or more magnetometers 160 can be any suitable magnetometer including, but not limited to, any suitable optically pumped magnetometer. Arrays of magnetometers are described in more detail herein. In at least some embodiments, at least one of the one or more magnetometers (or all of the magnetometers) of the system is arranged for operation in the SERF mode.

Figure 1B:
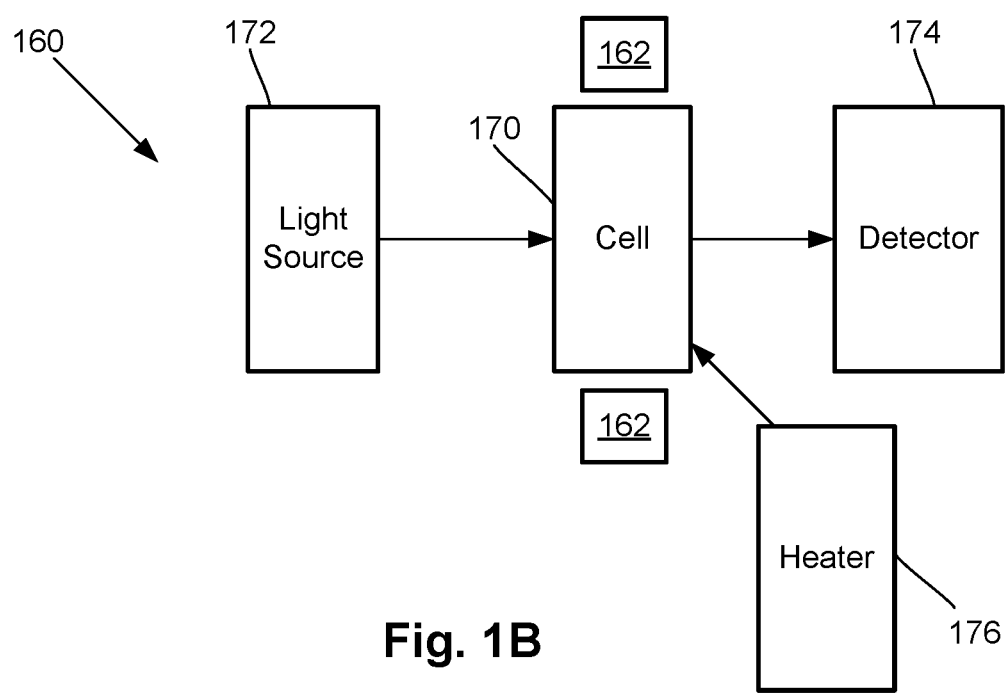
FIG. 1B is a schematic block diagram of one embodiment of a magnetometer, according to the invention.

FIG. 1B is a schematic block diagram of one embodiment of a magnetometer 160 which includes a vapor cell 170 (also referred to as a "cell" or "gas cell") such as an alkali metal vapor cell; a heating device 176 to heat the cell 170; a light source 172; and a detector 174. In addition, coils of a magnetic field generator 162 can be positioned around the vapor cell 170. The vapor cell 170 can include, for example, an alkali metal vapor (for example, rubidium in natural abundance, isotopically enriched rubidium, potassium, or cesium, or any other suitable alkali metal such as lithium, sodium, or francium) and, optionally, one, or both, of a quenching gas (for example, nitrogen) and a buffer gas (for example, nitrogen, helium, neon, or argon). In some embodiments, the vapor cell may include the alkali metal atoms in a prevaporized form prior to heating to generate the vapor.

The light source 172 can include, for example, a laser to, respectively, optically pump the alkali metal atoms and probe the vapor cell. The light source 172 may also include optics (such as lenses, waveplates, collimators, polarizers, and objects with reflective surfaces) for beam shaping and polarization control and for directing the light from the light source to the cell and detector. Examples of suitable light sources include, but are not limited to, a diode laser (such as a vertical-cavity surface-emitting laser (VCSEL), distributed Bragg reflector laser (DBR), or distributed feedback laser (DFB)), light-emitting diode (LED), lamp, or any other suitable light source. In some embodiments, the light source 172 may include two light sources: a pump light source and a probe light source.

The detector 174 can include, for example, an optical detector to measure the optical properties of the transmitted probe light field amplitude, phase, or polarization, as quantified through optical absorption and dispersion curves, spectrum, or polarization or the like or any combination thereof. Examples of suitable detectors include, but are not limited to, a photodiode, charge coupled device (CCD) array, CMOS array, camera, photodiode array, single photon avalanche diode (SPAD) array, avalanche photodiode (APD) array, or any other suitable optical sensor array that can measure the change in transmitted light at the optical wavelengths of interest.

Figure 2:
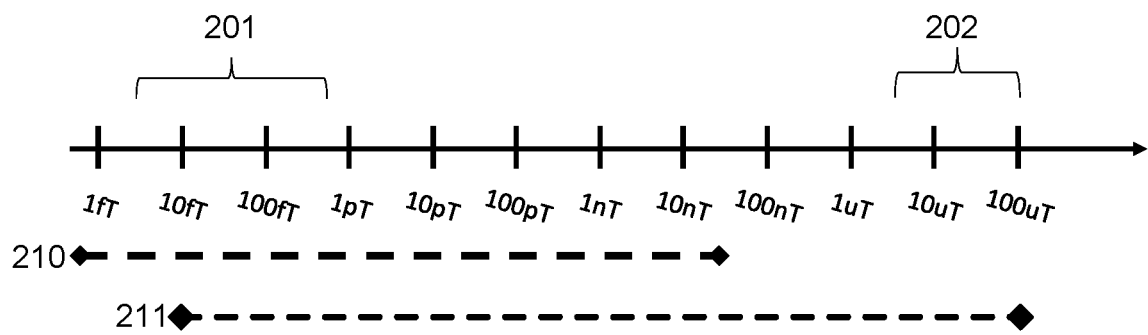
FIG. 2 shows a magnetic spectrum with lines indicating dynamic ranges of magnetometers operating in different modes.

FIG. 2 shows the magnetic spectrum from 1 fT to 100 µT in magnetic field strength on a logarithmic scale. The magnitude of magnetic fields generated by the human brain are indicated by range 201 and the magnitude of the background ambient magnetic field, including the Earth's magnetic field, by range 202. The strength of the Earth's magnetic field covers a range as it depends on the position on the Earth as well as the materials of the surrounding environment where the magnetic field is measured. Range 210 indicates the approximate measurement range of a magnetometer (e.g., an OPM) operating in the SERF mode (e.g., a SERF magnetometer) and range 211 indicates the approximate measurement range of a magnetometer operating in a scalar mode (e.g., a scalar magnetometer.) Typically, a SERF magnetometer is more sensitive than a scalar magnetometer but many conventional SERF magnetometers typically only operate up to about 0 to 200 nT while the scalar magnetometer starts in the 10 to 100 fT range but extends above 10 to 100 µT.

To facilitate accurate operation of a magnetic field measurement system, such as a MEG system, calibration of the magnetic field sensors (e.g., magnetometers) of the system can be useful or necessary. One prior calibration arrangement utilizes a combined hardware/software system for calibrating an on-scalp MEG sensor array (e.g., an array of magnetometers or other sensors) which is part of a system for determining the positions, orientations, and sensitivities of the on-scalp magnetic field sensors. This approach includes the use of driven coil loops that produce magnetic fields that may be approximated as magnetic dipoles. However, the coil loops are not positioned off the scalp and the relative locations and orientations of the coil loops are not well known. For example, the individual coil loops are affixed to the scalp. The coil loops are subsequently localized and the orientation of these coil loops is determined individually. As an example, a 3D digitizer pen is used to measure the coordinates of the corners of the individual plates upon which the coil loops are mounted. A Polhemus stylus digitizer pen can achieve 1 mm precision at best; however, a 2 mm error in measurement of the corners of a 2 cm baseline plate would cause the estimation of the plate orientation to be misrepresented by approximately six degrees (roughly $\arctan(1/10)$). In addition to imprecision in the machining of these plates and coil loops and inaccurate calibration of the driving current, errors in both the relative coil loop locations and orientations can negatively impact the model of each coil loop. Therefore, when using a non-linear optimization procedure to tune the magnetic field sensor calibration parameters so that the field measurements acquired by each magnetic field sensor align well with theoretical predictions of the measured valued of the magnetic fields sourced by each coil loop, these calibration errors can cause the model to differ from the truth.

Another prior calibration system utilizes a model of the magnetic field produced by field nulling coils (e.g., magnetic field generators) within OPM sensors. However, the magnetic fields produced by field nulling coils are relatively spatially complex in the region exterior to the OPM sensors and may be difficult to accurately model. The field nulling coils have a relatively large diameter and can have a relatively large deviation from a magnetic dipole approximation. In addition, the system does not utilize a rigid mounting body that would enable the relative locations and orientations of the driving currents for the field nulling coils to be known to high precision. This system may also be difficult to employ when a small number of magnetic field sensors are placed at opposite sides of the head. As an example, for a MEG sensor array with just two magnetic field sensors positioned on opposite sides of the head, a large driving current would be applied to the field nulling coil attached to one sensor in order to cause a strong signal in the other. Locally, this field will be very strong. During the period of field nulling coil activation, this field may render the measurements taken by the sensor at the location of the active field nulling coil unusable.

Another calibration systems uses MRI scans of experimental subjects to print fitted head casts with OPM sensor mountings. The geometry of these mountings can be known to high accuracy. Therefore, the MEG sensor arrays are not geometrically reconfigurable and no calibration is necessary. However, requiring 3D printed head casts based on accurate head geometry models may restrict the ability to quickly reconfigure a sensor array for other users and would likely not be suitable for a commercial system intended for tens or thousands (or more) of users.

In contrast to these earlier calibration systems, a calibration arrangement, system, or method can include an array of reference coil loops on a rigid structure that fits over or onto the array of sensors (e.g., magnetometers). As an example, in the case of a MEG sensor array with the head covered by an array of OPMs, the calibration arrangement may have a dome structure.

Figure 3A:
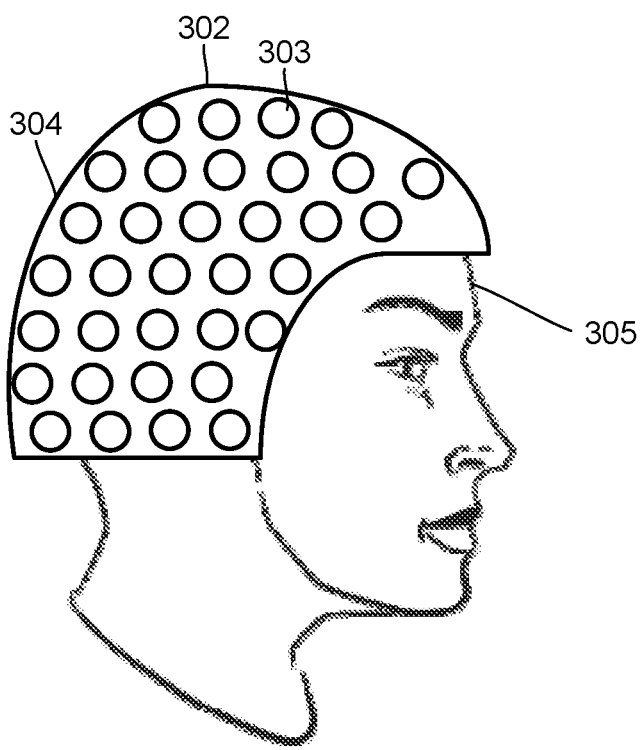
FIG. 3A is a schematic side view of one embodiment of a wearable magnetoencephalography (MEG) device worn by a user, according to the invention.

FIG. 3A illustrates a wearable MEG device 302 disposed on the head of a user 305. The wearable MEG device 302 includes multiple magnetic field sensors 303 (for example, OPM magnetometers, other magnetometers, or other magnetic field sensors) disposed on or in a sensor mounting body 304. The sensor mounting body 304 can take the form of, for example, a helmet, cap, hat, hood, scarf, wrap, or other headgear or any other suitable form, Further details discussing different form factors in small, portable, wearable devices and applications thereof are set forth in U.S. patent application Ser. Nos. 16/523,861; 16/457,655; and Ser. No. 16/364,338, and U.S. Provisional Patent Application Ser. Nos. 62/752,067; 62/829,124; 62/839,405; 62/894,578; 62/859,880; and 62/891,128 as well as other patents and patent applications cited herein, all of which are incorporated herein by reference in their entireties. In at least some embodiments, signals or data output from the magnetic field sensors 303 can be transmitted wirelessly.

Figure 3B:
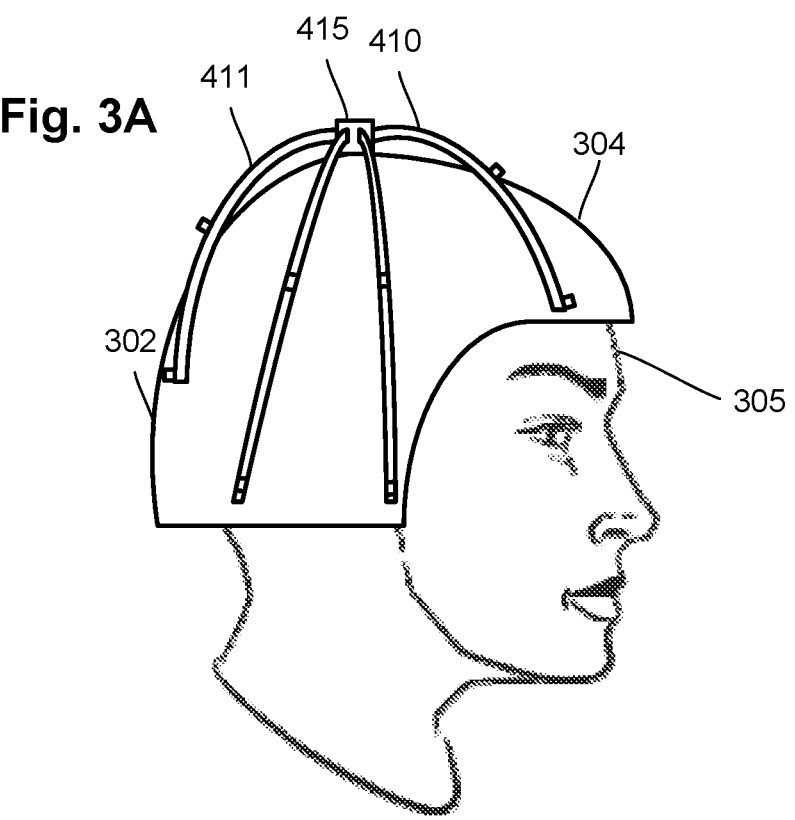
FIG. 3B is a schematic side view of one embodiment of a calibration arrangement attached to the MEG device of FIG. 3A, according to the invention.

FIG. 3B illustrates the wearable MEG device 302 (with the OPM sensors not shown) and a calibration arrangement 410 attached to the sensor mounting body 304 of the wearable MEG device. In at least some embodiments, the calibration arrangement 410 is detachable from the wearable MEG device 302. In at least some embodiments, the calibration arrangement 410 includes a mounting structure that can be attached to a MEG device 302 or other device. In at least some embodiments, the mounting structure of the calibration arrangement 410 is rigid. In at least some embodiments, the mounting structure of the calibration arrangement 410 is a unibody structure. As an example, the calibration arrangement 410 can be attached to the sensor mounting body 304 of a MEG device 302 that has magnetic field sensors (such as OPM sensors 303 or other magnetometers or sensors) which, at least in some embodiments, may be arranged in an unknown geometry or have unknown sensitivity. The calibration arrangement can reduce or eliminate potential errors in relative locations and orientations of the magnetic field sensors.

In at least some embodiments, the methods, calibration arrangements, or systems described herein can produce a number of mutually distinguishable magnetic fields with a known spatiotemporal pattern that enables an attached computing device (such as computing device 150 of FIG. 1A or a separated computing device) to perform software-based calibration for the geometrical and functional parameters of an array of magnetic field sensors (e.g., OPM sensors), such as a wearable MEG sensor array of the MEG device 302 of FIGS. 3A and 3B.

In at least some embodiments, a calibration arrangement 410 includes an array of reference coil loops. In at least some embodiments, the reference coil loops are distributed relatively evenly (or according to any other suitable distribution) across the scalp surface. In at least some embodiments, the reference coil loops are distributed so that each reference coil loop is at least 1, 2, 3, 4, or 5 centimeters from any single magnetic field sensor 303. In at least some embodiments, the reference coil loops are distributed, relative to the magnetic field sensors 303, to provide a magnetic field with a magnitude that is strong enough to give good SNR (signal-to-noise ratio) when detected by the magnetic field sensors.

Figure 4B:
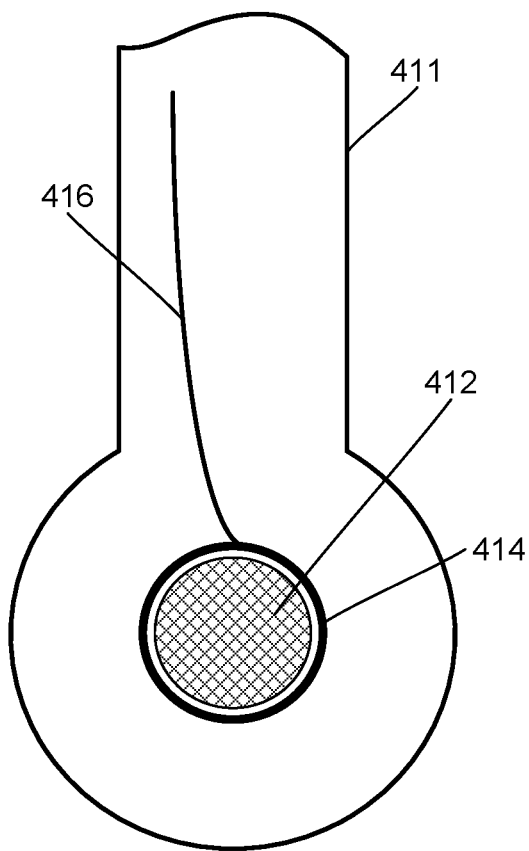
FIG. 4B is a schematic close-up view of a portion of the calibration arrangement of FIG. 4A, according to the invention.
Figure 4A:
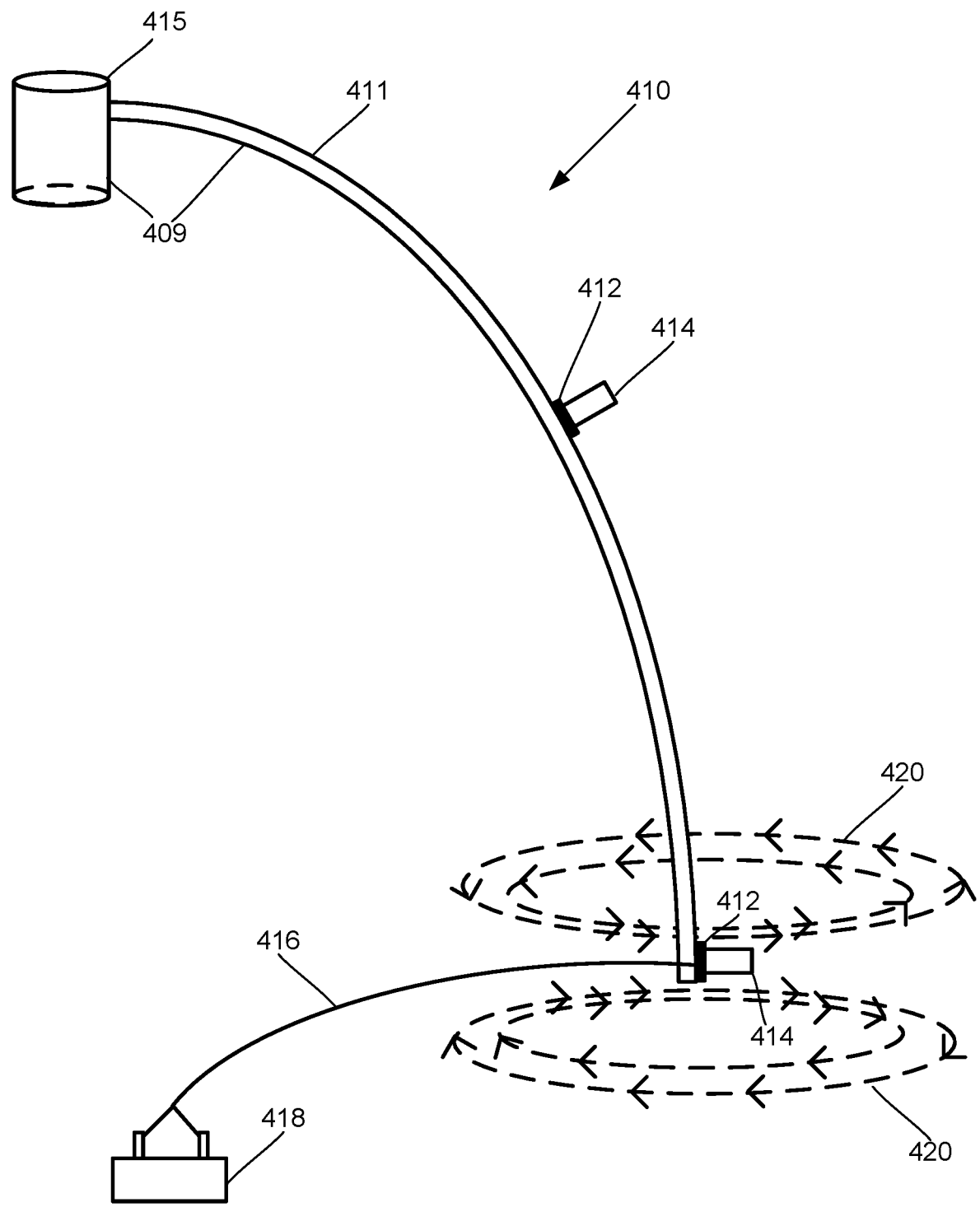
FIG. 4A is a schematic side view of a portion of one embodiment of a calibration arrangement, according to the invention.

FIG. 4A illustrates a portion of one embodiment of a calibration arrangement 410 that includes a rigid mounting body 409 having at least one attachment point nub 415 and, extending from the attachment point nub(s) and one or more mounting arms 411 (one mounting arm is illustrated in FIG. 4A and four mounting arms are illustrated in FIG. 3B). On each of the mounting arms are one or more winding nubs 414 with a reference coil loop 412 wound around each of the winding nubs. The calibration arrangement 410 can include one, two, three, or more attachment point nubs 415 and one, two, three, four, five, six, seven, eight, nine, ten, twelve, or more mounting arms 411. Each mounting arm 411 can include one, two, three, four, or more winding nubs 414 with a reference coil loop 412 associated with each winding nub. In some embodiments, each mounting arm 411 has the same number of winding nubs 414. In other embodiments, the mounting arms 411 may have different numbers or winding nubs 414. In some embodiments, each mounting arm 411 may have a same length. In other embodiments, the mounting arms 411 can have different lengths. In some embodiments, the winding nubs are omitted and the mounting arm 411 includes one or more reference coil loops 412.

In at least some embodiments, the calibration arrangement 410 can be fabricated in a modular fashion. For example, the calibration arrangement may allow one or more of the mounting arms 411 or attachment point nubs 415 to be added or removed (e.g., the mounting arms 411 or attachment point nubs 415 are detachable). In at least some embodiments, the winding nubs 414 or reference coil loops 412 may be detachable.

FIG. 4B illustrates one embodiment of a portion of a mounting arm 411 with a winding nub 414 and a reference coil loop 412. A pair of leads 416 extends from the reference coil loop 412, as illustrated in FIGS. 4A and 4B. In at least some embodiments, at least a portion of the leads 416 may be attached to, or pass through, a portion of the mounting arm 411 or may be entirely separate from the mounting arm 411. In at least some embodiments, the reference coil loops 412 or the leads 416 may be formed as conductive traces embedded within, or disposed on, the mounting arm 411. In at least some embodiments, a different pair of leads 416 is attached to each reference coil loop 412. In other embodiments, a pair of leads 416 may be attached to multiple reference coil loops 412.

The pair of leads 416 (for example, a twisted pair of leads), which are electrically coupled to one or more of the reference coil loops 412, are electrically connected to a driving current source 418, as illustrated in FIG. 4A. In at least some embodiments, the driving current source 418 is external to the remainder of the calibration arrangement 410. In other embodiments, the driving current source 418 may be disposed within the mounting body 409 of the calibration arrangement. In at least some embodiments that utilize multiple pairs of leads 416 that are each attached to individual reference coil loops 412 or sets reference coil loops, the driving current source 418 may include a processor or multiplexer in order to be capable of delivering different signals along the different pairs of leads.

In at least some embodiments, due to the knowledge of the physical arrangement of the components of the calibration arrangement 410, the non-target magnetic fields 420 produced by the driven reference coil loops 412 are known except for the determination of which of the two leads 416 attached to the reference coil loop 412 is positive and which is negative. In at least some embodiments, the positive and negative leads 416 of reference coil loops 412 can be defined in the following way: when the positive and negative leads are attached to the positive and ground terminals, respectively, of the driving current source 418 and a DC current is driven through the leads, the magnetic field produced by the reference coil loop 412 and measured at the top of the winding nub 414 is directed away from that reference coil loop 412, as illustrated in FIG. 4A. Therefore, the positive and negative leads 416 of each reference coil loop 412 may be determined by sampling the magnetic field vector at the top of that winding nub 414. Any other suitable definition of positive and negative can be used.

The calibration arrangement 410 with an array of reference coil loops 412 can be used with a sensor array (e.g., a MEG sensor array or an array of OPM sensors) for calibration of the sensor array such as, for example, calibration of the MEG device 302 of FIG. 3A. The rigid mounting body 410 is mounted (preferably rigidly mounted) upon a sensor mounting body 304 (see, FIG. 3A) of the MEG device 302 (or other magnetic field measurement device) at a primary attachment point in a manner that, preferably, ensures there are neither translational nor rotational degrees of freedom between the calibration arrangement 410 and the sensor mounting body 304.

Figure 5:
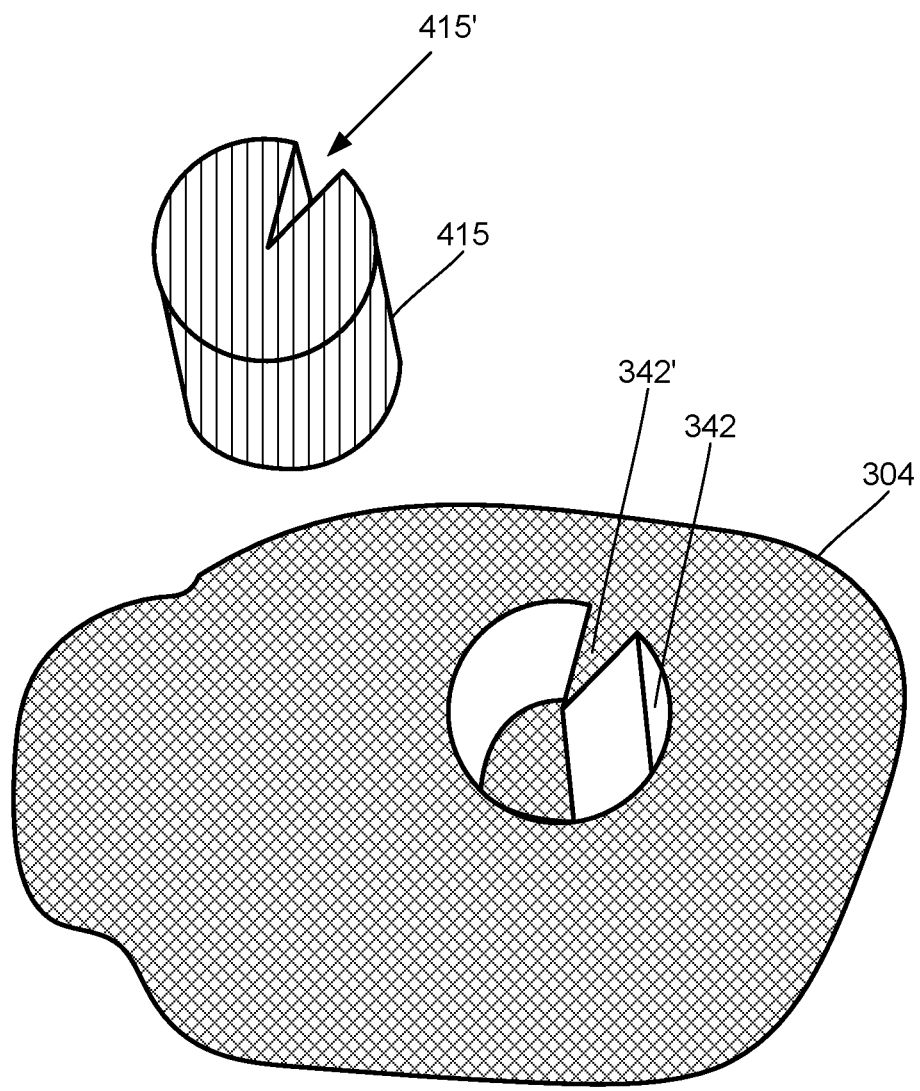
FIG. 5 is a schematic top view of portions of the MEG device of FIG. 3A and the calibration arrangement of FIG. 3B to illustrate attachment of the MEG device to the calibration arrangement, according to the invention.

FIG. 5 illustrates one embodiment of an attachment point nub 415 of a calibration arrangement 410 (FIGS. 3B and 4A—other elements of the calibration arrangement are omitted in FIG. 5 for clarity) that can be inserted into, or otherwise coupled to, a primary attachment point 342 (e.g., an attachment receptacle) on a sensor mounting body 304 of a MEG device 302 (FIG. 3A). In the embodiment illustrated in FIG. 5, the attachment point nub 415 fits into the primary attachment point 342, but in other embodiments, the primary attachment point 342 may be a protrusion that fits into or around the attachment point nub 415. Any other suitable attachment arrangement or mechanism between the primary attachment point 342 and the attachment point nub 415 can be used.

In at least some embodiments, the primary attachment point 342 of the sensor mounting body 304 and the attachment point nub 415 of the rigid mounting body 409 can possess strong angular asymmetry that only permits the primary attachment point 342 and the attachment point nub 415 to attach only at a single angle. As an example, in FIG. 5, the attachment point nub 415 includes a notch 415' with a correspondingly-shaped protrusion 342' in the primary attachment point 342. Alternatively or additionally, one or more secondary attachment points and second attachment point nubs can be provided to restrict rotation and translation of the sensor mounting body 304 of the MEG device 302 and the rigid mounting body 409 of the calibration arrangement 410. As an example, in addition to or as an alternative to the attachment point nub 415, one or more secondary attachment point nubs can be provided at the ends of one or more of the mounting arms 411 (or anywhere along the mounting arms) which can be used for attachment of the calibration arrangement 410 to the sensor mounting body 304 of the MEG device 302.

In at least some embodiments, the calibration arrangement 410 can be easily attached to, or removed from, the MEG device 302. In at least some embodiments, the primary and optional secondary attachment point(s) and attachment point nub(s) ensure there are neither rotational nor translational degrees of freedom between the calibration arrangement 410 and MEG device 302 to produce a repeatable configuration. Moreover, in at least some embodiments, the calibration arrangement 410 and MEG device 302 are arranged so that repeated attachments/removals do not impact calibration performance over time.

Once the calibration arrangement 410 and MEG device 302 are physically attached, the calibration arrangement 410 is ready to be used for the calibration routine. In at least some embodiments, the subject can be moving during calibration without affecting calibration performance. In at least some embodiments, the calibration arrangement 410 can be used and need not be adjusted while a subject is moving their head relative to the local surface of the earth. In at least some embodiments, fundamental limits on head movement are set by the magnetometer dynamic range. In at least some embodiments, although the calibration arrangement 410 can be attached to the MEG device 302 and thus co-moves with the head, the reference coil loops 412 are off the scalp and separated from the magnetic field sensors 303.

In at least some embodiments, the calibration arrangement 410 may be removed from the MEG device 302 after the calibration measurements have been acquired. In at least some embodiments, the aforementioned calibration procedure need not be complete before removal of the calibration arrangement 410. In at least some embodiments, the calibration arrangement 410 can remain attached to the MEG device 302 during measurement of neural signals. In at least some embodiments, the non-target reference magnetic fields 420 generated using the reference coil loops 412 of the calibration arrangement 410 can be present during the process of measuring target neural signals of the brain of the user. In at least some embodiments, a calibration arrangement 410 may enable continuous or periodic calibration of the MEG device 302 which could be valuable for MEG devices with the magnetic field sensors 303 whose calibration parameters change over the course of time.

In at least some embodiments, during a calibration procedure, currents are driven through the leads 416 to the reference coil loops 412 of the calibration arrangement 410 to generate non-target reference magnetic fields 420 and the magnetic field sensors 303 of the MEG device 302 measure the non-target reference magnetic fields. The resulting measurements can be uniquely associated to the reference coil loops 412 that produced each of the magnetic field contributions using a computing device (such as computing device 150 of FIG. 1A or another computing device) running calibration algorithm software. In at least some embodiments, the measurements can be uniquely associated with particular reference coil loops 412 by either driving currents to the individual reference coil loops with intensities that uniquely vary in time as, for example, a single sinusoidal function or, more generally, driving currents to the individual reference coil loops with intensities that uniquely vary in time in such a way that enables magnetic field measurements by the magnetic field sensors 303 to be decomposed uniquely into the contributions attributable to individual reference coil loops 412. In at least some embodiments, these unique associations can be observed in a frequency spectrum of the sensor measurements or using any other suitable method for identifying the individual magnetic fields generated by the reference coil loops 412.

In at least some embodiments, after decomposing the measured signals from the magnetic field sensors 303 into the components attributable to individual reference coil loops 412, reduction or minimization of the mismatch between the actual sensor measurements and theoretical or ideal sensor measurements can provide sensor calibration parameters. In this manner, a calibration can be obtained using the measured magnetic fields and expected measurements (e.g., theoretical or ideal measurements) based on a model of the reference coil loops. For example, a physics-based 'forward model' for the known reference magnetic fields generated using the reference coil loops 412 and known time-varying applied currents can be used to determine the calibration parameters for the individual magnetic field sensors 303. This reduction or minimization can be performed by a computing device (such as the computing device 150 of FIG. 1A or another computing device) running calibration algorithm software. Any suitable calibration algorithm can be employed in the software.

In at least some embodiments, to achieve more accurate estimation of the calibration parameters of each magnetic field sensor 303, one or more (or most of all) of the magnetic field sensors can measure high SNR signal contributions from multiple reference coil loops 412. In at least some embodiments, the locations and radii (or size) of the reference coil loops 412 are selected so that a magnetic field sensor 303 placed anywhere on the typical human scalp would receive high SNR signal contributions from at least two, three, four, or more of the reference coil loops. In at least some embodiments, the sensor mounting body 304 of the MEG device 302 is designed so that the locations of the reference coil loops 412 are at least one, two, three, four, or more cm from the nearest magnetic field sensor 303 when the calibration arrangement 410 is attached to the sensor mounting body 304. With a minimum distance of four centimeters in a prototype device, it was calculated that a 10 mA current amplitude passing through one of the reference coil loops 412 with a three mm radius produced a magnetic field having a magnitude at the magnetic field sensors 303 that does not exceed 1.5 nT.

In at least some embodiments, as the distance between the magnetic field sensors 303 and the reference coil loops 412 is increased, a magnetic dipole field of larger dipole moment should be generated to produce high SNR signal contributions in the magnetic field sensors. This may be desirable as a more distant magnetic dipole will, in general, produce a magnetic field with a maximum and minimum magnitude over a collection of the magnetic field sensors 303 that is more uniform. Because magnetic field sensors 303 (e.g., OPMs or other magnetometers) typically have an upper bound on the range in which the magnetic field sensors respond dynamically to a magnetic field, employing reference coil loops 412 at increased standoff distance may reduce the absolute number of reference coil loops 412 needed to ensure that each conceivable sensor location on the scalp receives usable, high-SNR signals from at least a selected number (e.g., two, three, or four) of reference coil loops.

In at least some embodiments, instead of using circular reference coil loops 412 that yield magnetic fields whose spatial configuration is dipolar, reference coil loops that produce other geometric magnetic field configurations may be employed including, but not limited to, reference coil loops with square, rectangular, or triangular geometries. For example, reference coil loops 412 that approximate current dipoles can be used.

In at least some embodiments, the ability to place reference coil loops 412 off the scalp but still co-moving with the head may mean that fewer reference coil loops need to be used because the magnetic dipole approximation used in modeling a reference current loop becomes a better approximation as a function of standoff distance, and fewer reference coil loops are needed to deliver magnetic fields to all the magnetic field sensors 303 that are neither too strong nor too weak.

In at least some embodiments, the use of circular reference coil loops 412 results in the simplicity of using the magnetic dipole approximations so that the reference magnetic fields can be modeled by less complex forward models. In at least some embodiments, simple forward models may also simplify non-linear optimization or calibration processes.

In at least some embodiments, the calibration methods and devices can work for MEG systems 302 having any number of the magnetic field sensors 303 placed anywhere on the scalp—even for a single sensor—and can be run concurrently with the collection of signals from neural sources using these magnetic field sensors. In at least some embodiments, the rigid mounting body 409 of the calibration arrangement 410 ensures that the geometrical arrangement of the array of reference coil loops 412 is known accurately.

Figure 6:
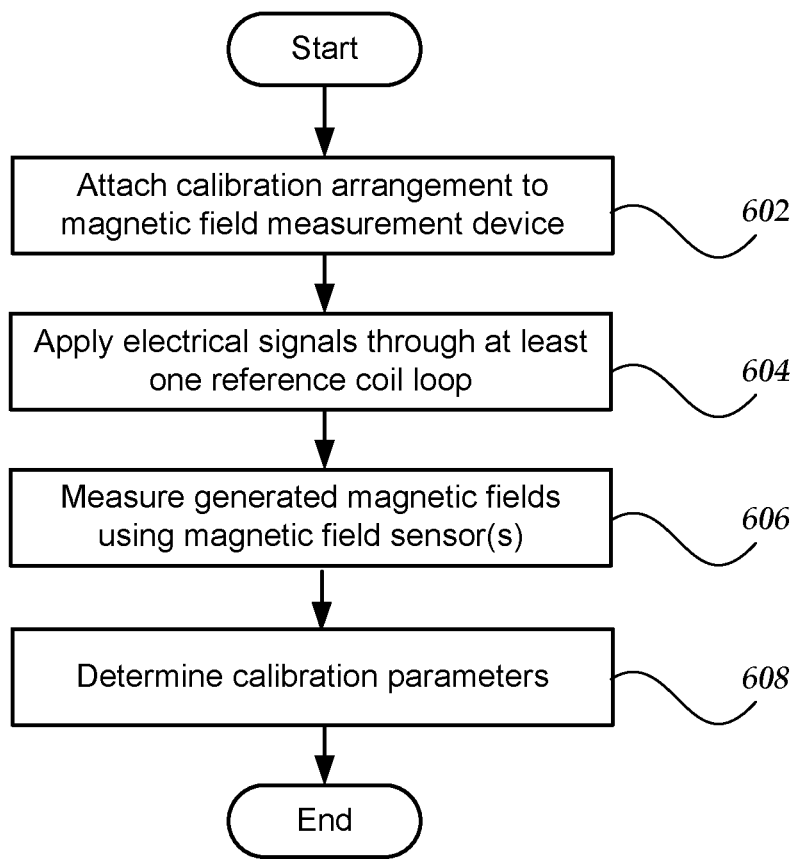
FIG. 6 is a flowchart of one embodiment of a method of calibrating a magnetic field measurement device, according to the invention.

FIG. 6 provides a flowchart of one embodiment of a method of calibrating a magnetic field measurement device such as the MEG device 302 of FIG. 3A. In step 602, the calibration arrangement (for example, the calibration arrangement 410 of FIG. 3B) is attached to the magnetic field measurement device. This attachment may be temporarily and may be reversible. Preferably, the attachment is reproducible and is rigid so that the calibration arrangement cannot translate or rotate relative to the magnetic field measurement device.

In step 604, electrical signals are application to one or more of the reference coil loops 412 of the calibration arrangement to generate magnetic field(s). In some embodiments, different electrical signals (for example, differing in frequency or temporal application) are applied to two or more of the reference coil loops 412 which may facilitate identifying which magnetic fields are generated by the individual reference coil loops. Other waveforms, such as those based on Legendre, Hermite, and Laguerre polynonials, can also be used.

In step 606, the generated magnetic fields are measured using one or more magnetic field sensors 303 of the magnetic field measurement device.

In step 608, calibration parameters are determined from the measured magnetic fields. In at least some embodiments, the resulting measurements can be uniquely associated to the reference coil loops 412 that produced each of the magnetic fields due to the use of different fields, as indicated above, which enables magnetic field measurements by the magnetic field sensors 303 to be decomposed uniquely into the contributions attributable to individual reference coil loops 412. In at least some embodiments, after decomposing the measured signals from the magnetic field sensors 303 into the components attributable to individual reference coil loops 412, reduction or minimization of the mismatch between the actual sensor measurements and theoretical or ideal sensor measurements can provide sensor calibration parameters.

Examples of magnetic field measurement systems in which the embodiments presented above can be incorporated, and which present features that can be incorporated in the embodiments presented herein, are described in U.S. Patent Application Publications Nos. 2020/0072916; 2020/0056263; 2020/0025844; 2020/0057116; 2019/0391213; 2020/0088811; 2020/005711; 2020/0109481; and 2020/0123416; U.S. patent application Ser. Nos. 16/573,394; 16/573,524; 16/679,048; 16/741,593; 16/752,393; 16/850,380 and 16/850,444, and U.S. Provisional Patent Application Ser. Nos. 62/689,696; 62/699,596; 62/719,471; 62/719,475; 62/719,928; 62/723,933; 62/732,327; 62/732,791; 62/741,777; 62/743,343; 62/747,924; 62/745,144; 62/752,067; 62/776,895; 62/781,418; 62/796,958; 62/798,209; 62/798,330; 62/804,539; 62/826,045; 62/827,390; 62/836,421; 62/837,574; 62/837,587; 62/842,818; 62/855,820; 62/858,636; 62/860,001; 62/865,049; 62/873,694; 62/874,887; 62/883,399; 62/883,406; 62/888,858; 62/895,197; 62/896,929; 62/898,461; 62/910,248; 62/913,000; 62/926,032; 62/926,043; 62/933,085; 62/960,548; 62/971,132; and 62/983,406, all of which are incorporated herein by reference in their entireties.

The methods, systems, and units described herein may be embodied in many different forms and should not be construed as limited to the embodiments set forth herein. Accordingly, the methods, systems, and units described herein may take the form of an entirely hardware embodiment, an entirely software embodiment or an embodiment combining software and hardware aspects. The methods described herein can be performed using any type of processor or any combination of processors where each processor performs at least part of the process.

It will be understood that each block of the flowchart illustrations, and combinations of blocks in the flowchart illustrations and methods disclosed herein, can be implemented by computer program instructions. These program instructions may be provided to a processor to produce a machine, such that the instructions, which execute on the processor, create means for implementing the actions specified in the flowchart block or blocks disclosed herein. The computer program instructions may be executed by a processor to cause a series of operational steps to be performed by the processor to produce a computer implemented process. The computer program instructions may also cause at least some of the operational steps to be performed in parallel. Moreover, some of the steps may also be performed across more than one processor, such as might arise in a multi-processor computer system. In addition, one or more processes may also be performed concurrently with other processes, or even in a different sequence than illustrated without departing from the scope or spirit of the invention.

The computer program instructions can be stored on any suitable computer-readable medium including, but not limited to, RAM, ROM, EEPROM, flash memory or other memory technology, CD-ROM, digital versatile disks ("DVD") or other optical storage, magnetic cassettes, magnetic tape, magnetic disk storage or other magnetic storage devices, or any other medium which can be used to store the desired information and which can be accessed by a computing device.

The above specification provides a description of the invention and its manufacture and use. Since many embodiments of the invention can be made without departing from the spirit and scope of the invention, the invention also resides in the claims hereinafter appended.

What is claimed as new and desired to be protected by Letters Patent of the United States is:

1. A calibration arrangement of a magnetic field measurement device, comprising:
   at least one attachment point nub configured for attachment to the magnetic field measurement device;
   a plurality of mounting arms extending from the at least one attachment point nub; and a plurality of reference coil loops distributed among the mounting arms, wherein each of the reference coil loops is attached to one of the mounting arms.

2. A magnetic field measurement system, comprising:
the calibration arrangement of claim 1; and
a magnetic field measurement device, comprising
a sensor mounting body,
a plurality of magnetic field sensors disposed on or within the sensor mounting body, and
at least one primary attachment point formed in or on the sensor mounting body and configured to receive the at least one attachment point nub of the calibration arrangement to attach the calibration arrangement to the sensor mounting body.

3. The magnetic field measurement system of claim 2, wherein each of the mounting arms comprises at least one winding nub disposed along the mounting arm with one of the reference coil loops disposed around each of the at least one winding nub.

4. The magnetic field measurement system of claim 2, wherein at least two of the reference coil loops are attached to one of the mounting arms.

5. The magnetic field measurement system of claim 2, wherein at least one of the mounting arms is reversibly detachable from the at least one attachment point nub.

6. The magnetic field measurement system of claim 2, wherein, when attached to the magnetic field measurement device, each of the reference coil loops is no closer than 1 centimeter from any of the magnetic field sensors of the magnetic field measurement device.

7. The magnetic field measurement system of claim 2, wherein, when attached to the magnetic field measurement device, each of the reference coil loops is no closer than 4 centimeters from any of the magnetic field sensors of the magnetic field measurement device.

8. The magnetic field measurement system of claim 2, wherein the at least one attachment point and the at least one primary attachment point nub have complementary features so that, when engaged, the complementary features resist rotation or translation of the calibration arrangement relative to the sensor mounting body.

9. The magnetic field measurement system of claim 8, wherein the complementary features comprise a notch and a corresponding protrusion.

10. The magnetic field measurement system of claim 2, wherein the calibration arrangement further comprises at least one secondary attachment point nub and the sensor mounting body further comprises at least one secondary attachment point configured to receive the at least one secondary attachment point nub.

11. The magnetic field measurement system of claim 2, further comprising a power source and leads coupling the reference coil loops to the power source.

12. The magnetic field measurement system of claim 11, further comprising a processor coupled to the power source and configured to apply different electrical signals to at least two of the reference coil loops.

13. The magnetic field measurement system of claim 12, wherein the processor is further coupled to the magnetic field sensors and configured to receive signals from the magnetic field sensors.

14. The magnetic field measurement system of claim 13, wherein the processor is further configured to decompose the received signals into components from each of the at least two of the reference coil loops based on at least one characteristic of the different applied electrical signals.

15. The magnetic field measurement system of claim 12, wherein the processor is further configured to determine calibration parameters using measured magnetic fields and expected measurements based on a model of the reference coil loops.

16. A method of calibrating a magnetic field measurement device, the method comprising:
attaching the calibration arrangement of claim 1 to the magnetic field measurement device;
applying electrical signals through a plurality of the reference coil loops; and
in response to the applied electrical signals, measuring magnetic fields generated by the reference coil loops using one or more magnetic field sensors of the magnetic field measurement device.

17. The method of claim 16, wherein attaching the calibration arrangement comprises receiving the at least one attachment point nub of the calibration arrangement in or on at least one primary attachment point of a sensor mounting body of the magnetic field measurement device.

18. The method of claim 16, wherein applying the electrical signals comprises applying different electrical signals to at least two of the reference coil loops.

19. The method of claim 18, further comprising decomposing the measured magnetic fields into components from each of the at least two of the reference coil loops based on at least one characteristic of the different applied electrical signals.

20. The method of claim 16, further comprising determining a calibration using the measured magnetic fields and expected measurements based on a model of the reference coil loops.

* * * * *